United States Patent
Zamoyski (12)

(10) Patent No.: US 6,486,146 B1
(45) Date of Patent: Nov. 26, 2002

(54) CANCER ACCELERANTS AND PHASE SYNCHRONIZATION METHODS

(76) Inventor: Mark Zamoyski, 988 Foothhill Dr., San Jose, CA (US) 95123

( * ) Notice: Subject to any disclaimer, the term of this patent is extended or adjusted under 35 U.S.C. 154(b) by 0 days.

(21) Appl. No.: 09/991,427

(22) Filed: Nov. 16, 2001

Related U.S. Application Data

(63) Continuation-in-part of application No. 09/490,722, filed on Jan. 25, 2000.

(51) Int. Cl.$^7$ .................. A61K 31/56; A61K 31/135
(52) U.S. Cl. ........................... 514/177; 514/651
(58) Field of Search ................... 514/177, 651

(56) References Cited

PUBLICATIONS

Harrison's Principles of Internal Medicine, McGraw Hill, 14$^{th}$ Edition, 1998, Fauci Et Al pp. 527–536, 564–566, 601, 2101.
Harrison's Principles of Internal Medicine, McGraw Hill, 15$^{th}$ Edition, 2001, Braunwald Et Al, pp. 530, 538–541, 576.
Physician's Desk Reference, 54$^{th}$ Edition, Medical Economics Company Inc., 2000 pp. 864, 1407, 2412–2418.
Biochemical Pathways, John Wiley & Sons, Inc 1999, Michal pp. 92, 94.
Molecular Biology of the Cell, Third Edition Garland Publishing, 1994 Alberts Et Al.
University of Pennsylvania Cancer Center, "Chemotherapy for Breast Cancer–Jun. 2000" 44 Articles Website Download.
"Chemotherapy Leads to Bone Loss" Science News vol. 160, Aug. 11, 2001 p. 89 Published by Science Service, Article by Damaris Christensen.

*Primary Examiner*—Zohreh Fay

(57) ABSTRACT

The invention discloses compositions and methods for increasing chemotherapeutic specificity to endocrine dependent cancers, and reducing systemic toxicity, through administration of endocrine hormones in conjunction with administration of phase specific chemotherapeutics. The invention also discloses why prior art phase specific chemotherapeutic regimens fail to achieve high cure rates for cancer. The failure relates to the Gompertzian acceleration, or reduction in cancer cell cycle time, induced by the chemotherapeutic reduction of tumor size, which in turn results in the cancer's lack of phase synchronicity to subsequent administrations of the phase specific chemotherapeutic(s). The invention discloses how to avoid this failure in endocrine dependent cancers by using endocrine blockers between chemotherapeutic administrations to halt the cancer cells from passing the S-Phase and then using endocrine hormones to restart and accelerate S-Phase progression in conjunction with administration of appropriate phase specific chemotherapeutic(s).

8 Claims, No Drawings

CANCER ACCELERANTS AND PHASE SYNCHRONIZATION METHODS

This is a continuation-in-part of Ser. No. 09/490,722 filed Jan. 25, 2000.

BACKGROUND-SUMMARY

Prior art has used endocrine downregulation therapy to downregulate the growth of endocrine dependent cancers. Present invention takes exactly the opposite approach, using endocrine upregulation to accelerate the growth of cancer in conjunction with administration of phase specific chemotherapeutics to increase tumor kill rates and reduce systemic toxicity over prior art.

Additionally, prior art has been unable to achieve high cure rates using phase specific chemotherapeutics in non endocrine dependent metastatic cancers as well. Applicant has discovered that the primary reason is prior art's failure to adjust the chemotherapeutic administration intervals for cancer's accelerated growth rate over successive chemotherapeutic administrations. This failure results in the cancer's return to an asynchronously cycling population which is mathematically a catastrophic event in the context of a phase specific administration regimen. Accordingly, applicant has disclosed methods for computing variable administration intervals that will keep the phase specific chemotherapeutic synchronized with the susceptible phase in the target cancer population. Alternatively, applicant has also disclosed methods of modulating the growth rate of endocrine dependent tumors by using endocrine hormones so as to keep a target cell population synchronized to a given administration regimen.

Definitions

As used in this application, the term "endocrine dependent cancer(s)" is used to mean cancers that have retained the functional hormone receptors normally present in the underlying tissue from which they arose and whereby cancer cells possessing these receptors will respond to administration of exogenous hormones by upregulating DNA synthesis. Examples of hormone receptors include, but are not limited to, estrogen receptors, progesterone receptors, and testosterone receptors.

BACKGROUND

Harrison's Principles of Internal Medicine (14th ed. p. 527–536) categorizes prior art drug treatments used for cancer into four broad categories Chemotherapy, Endocrine Therapy, Immunotherapy, and Hematopoietic Growth Factors. Chemotherapy relates to substances toxic to cancer. Endocrine Therapy relates to inactivating or inhibiting steroids produced by the body that promote growth of certain cancers. Immunotherapy relates to enhancing various aspects of the natural human immune system to inhibit growth of cancer. Hematopoietic Growth Factors focus on enhancing recovery of bone marrow products for patients receiving myelosuppressive chemotherapy. Chemotherapy and Endocrine therapy have relevance to present invention and as such a brief background of prior art is provided.

Prior Art Chemotherapeutics (HPIM 14th ed. pgs. 527–534)

Most chemotherapeutic agents in use today are cell cycle active; that is, they are cytotoxic mainly to actively cycling cells. In addition, some cell cycle active agents are phase specific; that is, they are cytotoxic to cells in a particular phase of the cell cycle.

Alkylating agents are among the most widely used anti tumor agents and are efficient at cross-linking DNA, leading to strand breakage. Alkylating agents include cyclophosphamide, ifosfamide, melphalan, busulfan, mechlorethamine (nitrogen mustard), chlorambucil, thiotepa, carmustine, lomustine as well as platinum compounds such as cisplatin and carboplatin, which are not true alkylating agents also lead to covalent cross linking of DNA. These agents are best regarded as cell-cycle active but non-phase specific.

Purine/pyrimidine analogs/antimetabolites induce cytotoxicity by serving as false substrates in biochemical pathways. They are cell cycle active and specific mainly for the S phase. They include cytarabine, fluorouracil, gemcitabine, cladribine, fludarabine, pentostatin, hydroxyurea, and methotrexate.

Topoisomerase inhibitors interfere with the enzymes topoisomerase 1 and topoisomerase 2, responsible for mediating conformational and topological changes in the DNA required during transcription and replication. These agents include daunorubicin, doxorubicin, idarubicin, etoposide, teniposide, dactinomycin, and mitoxantrone.

Plant Alkaloids include vincristine, vinblastine, and vinorelbine which inhibit microtubule assembly by binding to tubulin and docetaxel and paclitaxel which function by stabilizing microtubules and preventing their disassembly. They are cell cycle active and cytotoxic predominately during the M phase of the cell cycle.

Antitumor Antibiotics include bleomycin that induces DNA strand breakage through free radical generation and Mitomycin C which cross links DNA. They are cytotoxic mainly during the G2 and M phase.

Other Agents include dacarbazine and procarbazine which act as alkylating agents to damage DNA and L-Asparaginase, the only enzyme used as a anti tumor agent, which acts by depletion of extracellular pools of asparagine.

Chemotherapeutic agents exhibit a dose response effect. At sufficiently low concentrations no cytotoxicity is observed. At increasing concentrations, cell kill is proportional to drug exposure. At high concentrations, the effect reaches a plateau. Drugs that are cell cycle active, but not phase specific, such as alkylating agents, characteristically have steep dose response curves: An increase in the drug concentration by an order of magnitude or more results in a proportional increase in tumor cell kill. By contrast, the dose response curve of phase specific agents, such as the antimetabolites, typically is linear over only a narrow range. These agents are less suitable for dose escalation and increased tumor cell kill is observed after prolonged exposure as a larger percentage of the tumor cells enter the cell cycle.

Chemotherapy employs two principles in administration: Therapeutic Index Dosing and Cyclical Administration (HPIM 14th ed. 527–528 Pharmacodynamics section).

The therapeutic index represents the difference between the response of the tumor and response of normal tissue for a given dose of chemotherapeutic. Normal cells are also susceptible to the cytotoxic effects of chemotherapeutic drugs and exhibit a dose-response effect, but the response curve is shifted relative to that of malignant cells (see HPIM 14th ed. P. 528, FIGS. 86-3 enclosed). This difference represents the therapeutic index. The toxicity to normal tissue that limits further dose escalation is the "dose-limiting toxicity". The dose just below this point is the "maximum tolerated dose". Proliferative normal tissues such as the bone marrow and gastrointestinal mucosa are generally the most susceptible to chemotherapy-induced toxicity. The usefulness of many chemotherapeutics is limited by the fact that they have a narrow therapeutic index (HPIM 14th ed. p.527).

Tumor regression in response to chemotherapy is logarithmic. A given dose of chemotherapy kills a constant percentage of cells. The "cell kill rate" (CKR) as used in this application is hereby defined as the percentage of cells that are killed during one cell division cycle at a given dosage of chemotherapeutic. The "tumor kill rate" as used in this application is hereby defined as the percentage of cells of a tumor that are killed during one administration cycle of a chemotherapeutic, which is directly proportional to the CKR and the number of cell division cycles that occur over the chemotherapeutic's administration (or efficacy) period. As an example, if a 90% CKR chemo is administered over one cell division cycle, the tumor kill rate is also 90%. If the 90% CKR is administered over two cell division cycles the tumor kill rate is 99%. Conventional methods typically focus on "maximum tolerated doses" and extended administration periods.

Cyclical administration is required to allow normal rapidly proliferating cell populations to recover from the effects of chemotherapy. The number of administration cycles required to completely eradicate a tumor is dependent on the tumor kill rate of the therapeutic. To completely eradicate a tumor it is necessary to get below the mathematical 1 surviving cell number. As an example, to kill a 10 billion cell tumor with a chemotherapeutic that kills 95% of the tumor cells each administration cycle (5% survive) would require 8 cycles of chemotherapy (i.e. $10,000,000,000 \times 0.05 \times 0.05 \times 0.05 \times 0.05 \times 0.05 \times 0.05 \times 0.05 \times 0.05 = 0.39$). In contrast, a chemotherapeutic with a 50% tumor kill rate would require 34 administration cycles to get the 10 billion cell tumor below the one surviving cell number (i.e. $10,000,000,000 \times 0.5$ (34 times)=0.58). Likewise a 99% tumor kill rate would require only 6 administration cycles to get below the one surviving cell number.

Prior Art Endocrine Therapy (HPIM 14th ed. pgs. 534–535)

Endocrine therapy for hormone responsive malignancies depends on the presence of the appropriate hormone receptors, which in turn depends on the presence of those receptors (e.g. estrogen, progesterone, testosterone) in the underlying tissue from which the malignancy arose. Steroid hormones bind to specific intracellular receptors and induce a conformational change in the hormone-receptor complex that allows DNA transcription to proceed. Prior art hormonal antitumor agents are functional agonists or antagonists of the steroid hormones (HPIM 14th ed. p. 534).

The prior art use of endocrine therapy for malignancies possessing androgen, estrogen or progesterone receptors is presented in more detail by the specific cancers possessing these receptors.

Prostate Cancer: The androgen therapies for prostate cancer (HPIM 14th ed. p. 601) are all focused on reduction of androgen blood levels. The 4 methods under prior art are: 1) surgical castration and adrenalectomy to remove glands that produce androgens; 2) inhibition of pituitary gonadotropin and/or adrenocorticotropin production by estrogen therapy, hypophysectomy, or treatment with luteinizing hormone releasing hormone (LHRH) analogues such as Leuprolide or buserelin; 3) inhibition of androgen synthesis by the testes and adrenals (aminoglutethimide); and 4) inhibition of the binding of androgen to its receptor protein (cyproterone, flutamide, or bicalutamide).

Breast Cancer: Normal breast tissue contains both estrogen and progesterone receptors. Malignant breast tissue usually retain one or both of these phenotypes and methods for detecting the presence of these receptors is well established in prior art (HPIM 14th ed. p. 566). The Endocrine therapies for breast cancer are are grouped into 7 categories and summarized in Table 91-4 (HPIM 14th ed. p.566). They all focus on inhibiting endocrine dependent cancer cells from cycling by inhibiting or decreasing endogenous endocrine levels. 1) Castration removes the organs responsible for estrogen production, dropping endogenous estrogen levels and reducing the cancer's rate of growth. 2) Antiestrogens (e.g. tamoxifen) compete with estrogens at the receptors and thus act as inhibitors. 3) Progestogens are antiestrogenic. 4) Adrenalectomy is removal of the adrenal glands which decreases formation of estrogen precursors. 5) Aromatase inhibitors prevent aromatase from catalyzing reactions along several metabolic pathways involved in the synthesis of estrogens (BP p.94), thus reducing estrogen levels. 6) Hypophysectomy is surgical removal of the hypophysis or pituitary gland, thus reducing estrogen production by removing the upstream cascades that initiate its synthesis. And lastly, 7) additive androgen or estrogen therapy— androgens reduce estrogen by ablation of the ovaries (PDR p. 1407) and high estrogen concentrations stimulate 17β-hydroxysteroid dehydrogenase which converts estradiol (the most potent estrogen) into a much less active form as well as reducing progesterone receptor formation (BP p. 92).

HPIM 14th ed. p. 565 also discloses use of adjuvant regimens which are summarized in Table 91-3. Four of the six methods use combinations of chemotherapeutics only. The other two use Tamoxifen, either by itself or after chemotherapy. Tamoxifen competes with estrogen at the receptors and thus acts as an inhibitor (BP p.94), once again consistent with the prior art approach of inhibiting the growth of the endocrine dependent cancer. A further prior art search was performed by reviewing the list of 44 articles posted by the University of Pennsylvania Cancer Center Website titled "Chemotherapy for Breast Cancer", a copy of which is included under the IDS. The prior art articles were consistent with HPIM's disclosures. None of the studies proposed the use of endocrine cancer accelerants in conjunction with chemotherapeutics as proposed by present invention.

Additionally, prior art's fairly high dose chemotherapy alone causes endocrine downregulation through ablation of organs responsible for endocrine production. In a study of 49 women undergoing chemotherapy for early stage breast cancer, 71% were subsequently diagnosed with ovarian failure (Science News, vol. 160 p. 89). Ovaries produce estrogen. The early and rapid bone loss in these women further corroborated this under-appreciated side effect of chemotherapy, which also results in endocrine downregulation. The adverse effect of endocrine downregulation and subsequent unresponsiveness of tumors to chemotherapeutics because of the resulting "S-Phase Halt" will be discussed in more detail below. Use of cancer accelerants proposed by present invention will allow for much lower doses of chemotherapeutic which will also provide the novel benefit of preventing the inadvertent "chemotherapeutic castration" caused by prior art administration regimens.

In summary, all prior art endocrine therapies are used to inhibit cancer cells from cycling. The statement " . . . combinations of chemotherapy with endocrine therapy are not useful" (HPIM 14th ed. p. 566, Endocrine Therapy section) are correct in light of prior art. However, this statement will no longer be true under present invention. It will be shown that combinations endocrine hormones with chemotherapy can be extremely useful and yield novel benefits over prior art such as increased tumor kill rates, reduced systemic toxicity, and the ability to maintain chemotherapeutic-to-cancer phase synchronization.

Unobviousness Over Prior Art

The compositions and methods of present invention are not obvious over prior art because they are exactly opposite to prior art. Prior art teaches use of endocrine therapies to inhibit cancer growth. Present invention teaches use of endocrine therapy to accelerate cancer growth. Prior art endocrine therapy is not used concurrent with chemotherapy whereas current invention uses endocrine administration concurrent with administration of chemotherapeutic(s) and is integrally dependent on its interaction with said chemotherapeutics unlike prior art endocrine therapy.

Novelty and Utility Over Prior Art

"Cancer Accelerant" compositions and methods of present invention will yield a broad spectrum of new benefits over prior art including increased kill rate at a given dose of chemotherapeutic, or reduced dose of chemotherapeutic needed to achieve a given kill rate. Applicant will also show how to use endocrine accelerants to create user defined curative administration regimens, retain S-phase proportionality during chemotherapeutically induced accelerated growth, and how to create the 100% S-Phase tumor.

Additionally, applicant will disclose why prior art phase specific chemotherapeutic regimens are not curative but only moderately palliative. Corrected administration methods will be disclosed for maintaining phase specific chemotherapeutic-to-cancer phase synchronization in non endocrine dependent cancers. Applicant will also apply these corrected methods to endocrine dependent cancers, using endocrine accelerants to retain S-Phase proportionality and maintaining proper chemotherapeutic-to-cancer phase synchronization throughout the administration regimen. The novel compositions and methods disclosed will provide great utility over prior as they will yield curative versus palliative regimens.

The statement " . . . combinations of chemotherapy with endocrine therapy are not useful" will no longer be true under present invention.

Utility of Present Invention—Novel Mechanism of Action over Prior Art

The mechanism of action (MOA) of present invention has no comparable in prior art and can be summarized as follows: Current invention proposes releasing the brakes on the endocrine dependent cancer's S phase halt, or greatly upregulating DNA transcription, at just the right time to result in a several-fold increase in the amount of damage inflicted by chemotherapeutic(s) to cancer cells during said accelerated DNA replication period or subsequently during DNA separation (S phase and M Phases respectively). Applicant also uses this stop/start (i.e. slow/fast) potential to maintain chemotherapeutic-to-cancer phase synchronization.

S Phase Halt: Endocrine dependent cancers are different from other cancers in one significant respect. In endocrine dependent cells, mutations indigenous to a malignant cell drive the cell through G1 just like in any other cancer. The difference, however, comes in the S phase, since endocrine hormones are not indigenously produced by the malignant cell. DNA transcription requires the endocrine hormones produced by some other organ to dock with and activate appropriate nuclear endocrine receptors which in turn activate or upregulate DNA transcription. The relevant schematized pathway for estrogen, progesterone, and androgens for upregulating DNA transcription in the S-Phase is shown in Biochemical Pathways p. 227 FIGS. 17.6-2 enclosed (i.e. via Group A nuclear receptors). In the absence of hormone, an inhibitory protein (Hsp 90, possibly also Hsp 70 and Hsp 56) binds to the receptor and covers the DNA binding/dimerization domain. Hormone binding causes a conformational change in the receptor that results in the dissociation of the inhibitory protein, formation of homodimers, entry of the homodimers into the nucleus and binding to the palindromic DNA response element, interacting with TFIIB and accelerating formation of the pre-initiation complex of transcription.

When endocrine levels are low or absent, the S phase can become disproportionately long as DNA transcription is stalled or greatly slowed down (i.e. what applicant refers to as the "S Phase Halt"). In this situation, a tumor would appear to have a disproportionate amount of cells in the S Phase, which can readily be determined under prior art flow cytometry and indirect S-Phase assessments using antigens associated with the cell cycle such as PCNA and Ki67 (HPIM 14th ed. p. 564).

Preface to Examples—Cell Cycle Times and Cancer

The cell cycle time of normal rapidly proliferating cells (e.g. bone marrow, gastrointestinal stem cells, hair, and skin) is between 19 to 25 hours, in which time the cell spends ~45% of its time in the G1 Phase, ~32% in the S Phase, 18% in the G2 Phase and 5% of its time in the M Phase. Epithelial cells that line the lumen of the gut have an even shorter cell cycle time of ~11 hours (MBOC 896).

A tumor's cell cycle time is much longer by contrast. A typical tumor follows a Gompertzian growth curve (HPIM 15th ed . . . p. 530 FIGS. 84-1). In the fairly fast, non endocrine dependent tumor portrayed in the example, the growth from the first clinically detectable mass of 1 billion cells (~1 cubic cm) at day 100 to lethal burden of 1 trillion cells (~1 kg) at day 200 requires 10 cell cycles (i.e. 1 bil., 2, 4, 8, 16, 32, 64. 128, 256, 512, 1 tril) over a 100 day period which mathematically works out to a cell cycle time of 10 days (i.e. 100 days/10 cell cycles=10 days/cell cycle). The fastest growth rate occurs in the 50 days prior to the tumor reaching a clinically detectable mass and averages 2 days per cell cycle.

Non endocrine tumors such as colon cancer have a significantly longer cell cycle time than implied in the above representation. The colon cancer median survival of 6.5 months with only best supportive care (BSC) (PDR p. 2414) implies an ~19 day colon cancer cell cycle time (i.e. 6.5 mo.=195 days & ~10 cell cycles required from the first clinically detectable tumor of ~1 bil. cells to lethal burden at ~1 tril. cells=~19 days per cell cycle).

An endocrine dependent tumor can have an even longer cell cycle time. Although surgical removal of a tumor from the breast area and adjuvant chemotherapy is used as a first line of treatment for breast cancer, nearly half of patients treated for the apparently localized breast cancer develop metastatic disease. The median survival for metastatic disease to death for breast cancer is ~2 years (HPIM 14th ed . . . p. 566). Starting with a metastasis that was at a clinically undetectable mass of ~1 million cells (~1 $\mu$L) when the primary breast tumor was detected, lethal burden of the metastasis would be reached in ~20+ cell cycles over ~2 years implying a cell cycle time in the ballpark of ~30 days for the endocrine dependent metastatic cells. The similarity in duration of an endocrine dependent breast cancer's cell cycle time to the menstrual cycle is not likely to be a mere coincidence. Normal breast tissue contains both progesterone and estrogen receptors. FIGS. 337-5 from HPIM 14th ed. p. 2101 shows the natural progesterone and estradiol levels over a menstrual cycle. A double peak of both estradiol and progesterone occurs only once a month around 24 days after start of menses. This likely acts as a natural, once a month, "brake release" on the S-Phase Halt which would also effect malignant breast cells that retained the progesterone and estrogen receptors.

Prior art endocrine downregulation/endocrine blocking therapies can extend the median survival to ~4 years ( 3–5 or more per HPIM 14th ed . . . p. 566). Doubling the median survival time means doubling the cell cycle time from roughly 30 day to 60 days. Since, endocrines function in the S-Phase, the additional 30 day cell cycle extension would manifest itself as an unusually large proportion of cells stuck in the S-Phase.

The difference between the 19 day non-endocrine dependent colon tumor, the 30 day endocrine dependent breast tumor and the 60 day endocrine blocked tumor is outlined in TABLE 1 below as it will be used for illustrative purposes in some examples, particularly in determining frequency of administration. TABLE 1 starts with the colon tumor cell cycle of 19 days and displays the number of days it takes a cell to get through that phase as well as the corresponding % of cells one would expect to be in a given phase at any given time, based on the normal cell cycle phase distribution and before any chemotherapeutic administration regimen. The endocrine dependent tumors use the colon cancer model as a baseline and add any additional cell cycle time into the S-Phase as this is the phase where the lack of endocrines has an effect, both naturally in the 30 day breast cancer and artificially in the 60 day endocrine blocked tumor.

TABLE 1

Comparative Tumor Profiles

| Phase | Colon | | Breast | | Breast (E-block) | |
|---|---|---|---|---|---|---|
| | Days | % cells | Days | % Cells | Days | % Cells |
| G1 | 8.5 | 45% | 8.5 | 28% | 8.5 | 14% |
| S | 6.0 | 32% | 17.0 | 57% | 47.0 | 78% |
| G2 | 3.5 | 18% | 3.5 | 12% | 3.5 | 6% |
| M | 1.0 | 5% | 1.0 | 3% | 1.0 | 2% |
| Totals | 19.0 | 100% | 30.0 | 100% | 60.0 | 100% |

Chemotherapy is a balancing act between toxicity to the tumor and toxicity to normal rapidly proliferating cells in the body. The slower rate of tumor cell cycling (10 days to 30 days) versus ~1 day for normal rapidly proliferating cells has been a major impediment to effective treatment of tumors under prior art. Present invention will show how to get around this issue.

Reduction to Practice—Redefining Administration Intervals

Due in part to the novel methods of present invention which use phase specific chemotherapeutics and in part to the inability of prior art to define or implement proper methods of using phase specific chemotherapeutics, it is also necessary to define novel methods for computing appropriate administration intervals for use with phase specific chemotherapeutics. This method will yield curative results versus prior art's palliative results.

Prior art tends to favor high dose regimens administered several weeks apart. There is no rational basis for doing this and mathematically it can never provide a curative result. To the contrary, present invention favors the lowest dose that will induce a desired kill rate in the phase (i.e. 95–100%) and has the shortest in vivo efficacy time (i.e. shortest terminal half life) and administration that is rationally synchronized with respect to the cancer cell cycle. The optimal phase specific chemotherapeutic under present invention should induce a kill rate in the phase of ~95–100% and have an in vivo efficacy period (terminal half life) of 3 or 4 hours to minimize systemic cytotoxicity.

The major flaw in prior art is that it erroneously uses a fixed administration interval (AI), usually based on some calendar schedule. A variable AI is required to adjust for the accelerated tumor growth and proportionately reduced cell cycle and phase times as the tumor moves backward along the Gompertzian growth curve (HPIM 15th ed . . . p. 530 FIGS. 84-1) over the course of a chemotherapeutic regimen. Without this adjustment the AI will very quickly be much greater than both the cancer cell cycle time, susceptible Phase time, and most importantly administration of the chemotherapeutic will no longer be appropriately synchronized to the cancer cell population.

The Gompertzian growth curve shows a fairly abrupt growth rate change on either side of the 1 billion cell level. Below that level a tumor grows up to 5 times faster than above it. Cancer is the accumulation of about half dozen or so genetic "accidents" or lesions in proto-oncogenes and/or tumor suppressor genes. So far about 60 proto-oncogenes (MBOC 1279) have been discovered and presumably there are roughly as many tumor suppressor genes. Examples of proto-oncogene products include practically every type of molecule involved in growth from protein growth factors, growth factor receptors, growth signal transduction molecules, to gene regulatory proteins. Growth is a balancing act where normally inhibitory influences predominate. Cancer's oncogenes and/or defective tumor suppressor genes tip the balance to where growth predominates. As tumor cells grow they become crowded and starved of oxygen an nutrients, causing them to upregulate production of angiogenic growth factors ( a process normal to all cells under such conditions) and neovascularize the tumor. Endothelial cells (i.e. blood vessel cells) however are not mutated and are still subject to growth controls (such as density dependent inhibition of cell division vial P27 Kip 1 upregulation) which means they will eventually slow or stop angiogenesis, especially in particularly crowded areas, even in light of the high levels of angiogenic factors issued by the crowded tumor cells. As tumor cells crowd each other beyond a certain point they can no longer get enough nutrients to sustain their overexpression of growth related proteins, angiogenic growth factors, or the 2,000 to 5,000 other structural and regulatory proteins required for cell growth and division.

Of critical relevance to present invention is understanding what happens when a chemotherapeutic hits a tumor like the one described above. Wiping out a large part of the crowded tumor is a windfall for the surviving cells. They now find themselves in a well neovascularized, oxygen and nutrient rich, empty space. Add to that a genetic mutation profile that is permanently switched on for growth and they will immediately resume fulfilling their genetic destiny. This will manifest itself as them resuming their earlier accelerated growth (or possibly even faster) until they have once again crowded themselves to the point of a lower growth rate.

In our colon cancer example, that would imply the 19 day cancer cell cycle time above the 1 Bil. cell level becomes a 3.8 day cell cycle time after a chemotherapeutic reduces the tumor's size below the 1 bil. cell level. Using a typical S-Phase chemotherapeutic which kills 100% of cells in the S-Phase, for a total tumor kill rate of 32%, the surviving cancer cells will be able to run through nearly 2 cell cycles (i.e. quadruple) before the next dose on chemotherapeutic is administered on day 7. In reality, this will never happen because well before they complete even 1 cycle the cell mass will once again reach the 1 billion mark and downregulate itself to the 19 day cell cycle.

When an AI becomes longer than the susceptible phase of the cycle, cells slip through the phase into non susceptible phases. When the AI becomes longer than the cell cycle itself, one or more cell cycles of the cancer can occur before the next chemotherapeutic administration. Regrowth, or even accelerated growth, results in the cancer cell population being phase asynchronous again, which is a catastrophic event for a phase specific administration regimen. AI's of a phase specific chemotherapeutic must precisely follow the phase progression of the cancer cells through the cycle, with each successive administration of chemotherapy occurring shortly before each successive batch of cells that entered the susceptible phase during the administration interval have had time to exit into a non susceptible phase. The return to an asynchronously cycling population will mathematically yield a result over time that is basically indistinguishable from using a non phase specific chemotherapeutic with a kill rate equal to the phase kill rate of the chemotherapeutic times the percent of cell in that phase—which at a best case 100% S-Phase kill rate times the 32% of cells in S-Phase is comparable to a non phase specific chemotherapeutic with a paltry 32% kill rate.

As an example, the studies of Camptosar® follow the prior art administration methods of using a fixed AI. TABLE 2 below was constructed from Study 3 (PDR p. 2413 Table 2) and shows the mathematically predicted progression of the tumor from the first clinically detectable mass to lethal burden for best supportive care as well as under the two different administration regimens used in Study 3. The 125 mg dose was administered once every 7 days for 4 weeks, followed by 2 weeks off for 4 months (3 cycles). The 100 mg dose was administered in the same manner but for only 3 months (2 cycles). In TABLE 2 below, the tumor's typical exponential growth rate has been computed using the equation: (starting # of cells)$\times 2^{(\Delta t/19)}$; where $\Delta t$ the relevant time period in days and 19 days is the colon cancers self limiting growth rate cell cycle. Tumor regression was computed using 32% of cells being killed each administration as if with a non phase specific chemotherapeutic. The mathematical model projects a lethal burden for the 125 mg regimen somewhere between 315–322 days compared to the 321 days (10.7 mo.×30 days) median survival observed, and projects lethal burden for the 100 mg dose at between 273–280 days compared to 279 days (93 mo.×30 days) median survival observed. The math supports that this S-Phase chemotherapeutic has a close to 100% S-Phase kill rate at both doses, however in the absence of the proper AI results in only modest palliative rather than curative affect.

TABLE 2

Tumor Size Until Lethal Burden (in # of cells)
(mathematical model using 32% kill rate)

|  | DAY | WEEK | NO CHEMO | 125 MG/M$^2$ | 100 MG/M$^2$ |
| --- | --- | --- | --- | --- | --- |
| start | 0 | 0 | 0 | 1,000,000,000 | 1,000,000,000 | 1,000,000,000 |
| Chemo | 1 | 0 | 0 |  | 680,000,000 | 680,000,000 |
| Regrow | 1 | 7 | 1 | 1,290,939,198 | 877,838,655 | 877,838,655 |
| Chemo | 2 | 7 | 1 |  | 596,930,285 | 596,930,285 |
| Regrow | 2 | 14 | 2 | 1,666,524,013 | 770,600,704 | 770,600,704 |
| Chemo | 3 | 14 | 2 |  | 524,008,478 | 524,008,478 |
| Regrow | 3 | 21 | 3 | 2,151,381,172 | 676,463,085 | 676,463,085 |
| Chemo | 4 | 21 | 3 |  | 459,994,898 | 459,994,898 |
| Regrow | 4 | 28 | 4 | 2,777,302,285 | 593,825,444 | 593,825,444 |
| Chemo | 5 | 28 | 4 |  |  |  |
| Regrow | 5 | 35 | 5 | 3,585,328,385 | 766,592,543 | 766,592,543 |
| Chemo | 6 | 35 | 5 |  |  |  |
| Regrow | 6 | 42 | 6 | 4,628,440,949 | 989,624,362 | 989,624,362 |
| Chemo | 7 | 42 | 6 |  | 672,944,566 | 672,944,566 |
| Regrow | 7 | 49 | 7 | 5,975,035,847 | 868,730,519 | 868,730,519 |
| Chemo | 8 | 40 | 7 |  | 590,736,753 | 590,736,753 |
| Regrow | 8 | 56 | 8 | 7,713,407,984 | 762,605,230 | 762,605,230 |
| Chemo | 9 | 56 | 8 |  | 518,571,556 | 518,571,556 |
| Regrow | 9 | 63 | 9 | 9,057,540,716 | 669,444,349 | 669,444,349 |
| Chemo | 10 | 63 | 9 |  | 455,222,157 | 455,222,157 |
| Regrow | 10 | 70 | 10 | 12,854,579,625 | 587,664,127 | 587,664,127 |
| Chemo | 11 | 70 | 10 |  |  |  |
| Regrow | 11 | 77 | 11 | 16,594,480,711 | 758,638,656 | 758,638,656 |
| Chemo | 12 | 77 | 11 |  |  |  |
| Regrow | 12 | 84 | 12 | 21,422,465,620 | 979,356,378 | 979,356,378 |
| Chemo | 13 | 84 | 12 |  | 665,962,337 |  |
| Regrow | 13 | 91 | 13 | 27,665,100,585 | 859,716,886 | 1,264,289,538 |
| Chemo | 14 | 91 | 13 |  | 584,607,482 |  |
| Regrow | 14 | 98 | 14 | 35,701,053,368 | 754,692,714 | 1,632,120,922 |
| Chemo | 15 | 98 | 14 |  | 513,191,046 |  |
| Regrow | 15 | 105 | 15 | 46,087,889,201 | 662,498,437 | 2,106,968,874 |
| Chemo | 16 | 105 | 15 |  | 450,498,937 |  |
| Regrow | 16 | 112 | 16 | 59,496,662,721 | 581,566,736 | 2,719,968,708 |
| Grow |  | 119 | 17 | 76,806,574,053 | 750,767,296 | 3,511,314,222 |
| Grow |  | 126 | 18 | 99,152,617,105 | 969,194,931 | 4,532,893,166 |
| Grow |  | 133 | 19 | 128,000,000,000 | 1,251,171,727 | 5,851,689,468 |
| Grow |  | 140 | 20 | 165,240,217,337 | 1,615,186,626 | 7,554,175,308 |
| Grow |  | 147 | 21 | 213,315,073,638 | 2,085,107,728 | 9,751,981,013 |
| Grow |  | 154 | 22 | 275,376,790,072 | 2,691,747,298 | 12,589,214,547 |
| Grow |  | 161 | 23 | 355,494,692,509 | 3,474,882,098 | 16,251,910,531 |
| Grow |  | 168 | 24 | 458,922,033,223 | 4,485,861,508 | 20,980,228,346 |
| Grow |  | 175 | 25 | 592,440,441,489 | 5,790,974,458 | 27,084,199,153 |
| Grow |  | 182 | 26 | 764,804,588,367 | 7,475,795,922 | 34,964,054,332 |
| Grow |  | 189 | 27 | 987,316,221,893 | 9,650,797,991 | 45,136,468,256 |

TABLE 2-continued

Tumor Size Until Lethal Burden (in # of cells)
(mathematical model using 32% kill rate)

|  | DAY | WEEK | NO CHEMO | 125 MG/M$^2$ | 100 MG/M$^2$ |
|---|---|---|---|---|---|
| Grow | 196 | 28 | 1,274,565,211,611 | 12,458,593,418 | 58,268,436,129 |
| Grow | 203 | 29 |  | 16,083,286,595 | 75,221,008,202 |
| Grow | 210 | 30 |  | 20,762,545,097 | 97,105,747,997 |
| Grow | 217 | 31 |  | 26,803,183,315 | 125,357,616,435 |
| Grow | 224 | 32 |  | 34,601,279,971 | 161,829,060,818 |
| Grow | 231 | 33 |  | 44,668,146,613 | 206,911,477,977 |
| Grow | 238 | 34 |  | 57,663,863,945 | 269,692,015,821 |
| Grow | 245 | 35 |  | 74,440,542,271 | 348,155,994,597 |
| Grow | 252 | 36 |  | 96,098,213,934 | 449,448,220,426 |
| Grow | 259 | 37 |  | 124,056,951,221 | 580,210,325,195 |
| Grow | 266 | 38 |  | 160,149,981,109 | 749,016,251,848 |
| Grow | 273 | 39 |  | 206,743,888,164 | 966,934,439,410 |
| Grow | 280 | 40 |  | 266,893,789,167 | 1,248,253,569,680 |
| Grow | 287 | 41 |  | 344,543,654,124 |  |
| Grow | 294 | 42 |  | 444,784,908,513 |  |
| Grow | 301 | 43 |  | 574,190,273,055 |  |
| Grow | 308 | 44 |  | 741,244,730,566 |  |
| Grow | 315 | 45 |  | 956,901,877,960 |  |
| Grow | 322 | 46 |  | 1,235,302,142,848 |  |

Present invention proposes a method of administering phase specific chemotherapeutics using an administration interval defined by the equation:

$$AI = (DCCC) \times (\% \, CIP) \times (CF)$$

Where:

AI=Administration Interval (in days)

DCCC=Duration of the Cancer Cell Cycle (in days)

% CIP=the percentage of cancer Cells in the Phase in which the chemotherapeutic exhibits toxicity (e.g. determined by flow cytometry for S-Phase)

CF=Confidence Factor, which is a number between 0 and 1, preferably between 0.6–0.8 that reduces the AI to account for margin of averaging error Note: Any suitable time increment may be used, e.g. days may be substituted with hours as long as the same time increment is used for all variables Note: The equation may be also written as AI=(Duration of Relevant Phase in days)(CF)

EXAMPLE

Using the above method in the colon cancer example with an S-Phase chemotherapeutic the first Administration Interval, assuming an initial tumor mass of at least 2 bil. cells, would have been computed under present invention as:

$$AI = (DCCC) \times (\% \, CIP) \times (CF)$$

$$AI = (19 \, days) \times (32\% \, of \, Cells \, in \, the \, S \, Phase) \times (0.8)$$

$$AI = (6.08 \, days) \times (0.8)$$

$$AI = \sim 5 \, days$$

Present invention also computes the minimum consecutive number of administrations as:

$$\#Admins = (DCCC \div AI) \times (1 \div CF)$$

$$= (19 \, days \div 5 \, days) \times (1 \div .8)$$

$$= \sim 5 \, administrations$$

Present invention's 5 administrations, spaced AI days apart constitute one administration cycle as defined per the Skipper log cell kill model. Additional cycles need to be added if there is are several masses of varying size because smallest masses will still be asynchronous until the start of the shorter AI intervals.

Reduction to Practice Example of Phase Synchronized Growth Rate Adjusted AI

It is critical to note that the equation provided under present invention is dynamic. As the tumor shrinks, it accelerates its growth rate as it slides back along the Gompertzian growth curve (HPIM 15th ed . . . p. 530 FIG. 84-1) and the equation for AI is computed, in advance, using a shrinking DCCC value based on growth rates/reduced cell cycle times projected moving backward along the curve. As a simplified example, using the Gompertzian curve from HPIM, above the 1 Bil. cell mass the colon cancer previously described grows at its 19 day cell cycle and below the 1 Bil. cell mark it grows roughly 5 times faster, or at a 3.8 day cell cycle. If we start with an observed tumor of ~2 cubic cm (2 Bil. cells), the first chemo administration would wipe out ~100% of the 32% of cells in the S-Phase leaving 68% surviving tumor cells that were in all other phases, or 1.36 Bil. cells. Thus the AI between the first and second administration would be computed as previously done at 5 days. This second administration would now be expected to put the tumor below the 1 bil. cell number where the growth rate increases five fold to a 3.8 day cycle, and using the AI formula of present invention would dictate a 1 day interval between the second and third administrations (i.e. AI=3.8 days×32%×0.8 confidence factor=~1 day). This would apply through the remainder of the administrations. Thus, one administration cycle of the S-phase chemotherapeutic would consist of giving the chemo on days 1, 6, 7, 8, 9 for the tumor described.

Alternatively, methods can be employed to maintain the stability of the tumor growth rate or modulate the duration of the tumor's phase, obviating the need for a variable AI. As an example, in one of the reduction to practice examples presented below, applicant will disclose methods for modulating the duration of the S-phase in endocrine dependent tumors by using tamoxifen to slow down the S-phase and endocrine "cancer accelerants" of present invention such as estradiol, progesterone, or androgens to speed up the S-phase. By modulating the duration of the S-Phase in this way it will not only allow for a fixed AI but makes it possible to artificially alter variables such as DCCC and % CIP in the above equation to create a user chosen AI (within parameters).

It will also be possible in the near future to selectively halt proliferation of both angiogenesis and certain non endocrine dependent neoplasms simultaneously by compositions and methods filed for by applicant under separate patent applications.

Having defined the proper way to compute AI over prior art it is now possible to proceed with meaningful examples of using "cancer accelerants".

SUMMARY OF THE INVENTION

The present invention provides compositions and methods for treating cancers possessing endocrine receptors by administration of endocrine hormones in conjunction with administration of phase specific chemotherapeutics.

Invention also discloses methods for insuring synchronization of phase specific chemotherapeutics to the susceptible phase in the cancer cell population over successive chemotherapeutic administrations. Additionally, invention also discloses methods for synchronizing the susceptible phase in the cancer cell population to the administration of phase specific chemotherapeutics.

OBJECTS OF INVENTION

It is an object of the invention to increase the tumor response rate to a given dose of chemotherapeutic(s).

It is an object of the invention to increase the kill rate of a given dose of chemotherapeutic(s).

It is an object of the invention to reduce the amount of chemotherapeutic(s) required to achieve a given kill rate.

It is an object of the invention to reduce the amount of chemotherapeutic(s) required to achieve a given tumor response rate.

It is an object of the invention to reduce systemic cytotoxicity, including but not limited to preventing ablation of ovaries or testes, reduction in hematologic toxicity, and reduction in the amount of gastrointestinal cells destroyed.

It is an object of the invention to provide novel methods of computing administration intervals for phase specific chemotherapeutics that result in curative effects versus palliative effects.

It is an object of the invention to provide a novel phase specific administration regimen that is synchronized with the cell cycle time of the cancer in a manner to provide much greater tumor response and median survival rates over prior art methods.

DETAILED DESCRIPTION OF THE INVENTION

The treatments disclosed below involve administration of endocrine hormones in conjunction with administration of phase specific chemotherapeutics. Materials and methods for achieving this are described below.
Reduction to Practice—Endocrine Hormones for Use in Present Invention A large variety of estrogen, progesterone, or testosterone hormones are commercially available and are listed in the Physician's Desk Reference (PDR), incorporated herein by reference. As an example, for cancers exhibiting estrogen receptors one could use estrogens comprising, Estradiol Tablets (Mylan or Watson), Premarin® Intravenous estrogens (Wyeth-Ayrest), Premarin® estrogen tablets (Wyeth-Ayrest) Estratab® esterified estrogens tablets (Solvay), any one of several transdermal estrogen delivery systems, or any other suitable estradiol, estriol, estrone, or estrogen substitute or synthetic estrogen such as ethinylestradiol, or diethylstilbestrol, or any suitable means of increasing endogenous estrogen levels, or any combination of the aforementioned. As an example for cancers also exhibiting progesterone receptors one could use Prometrium® capsules (Solvay) or any other suitable progesterone substitute or any suitable means of increasing endogenous progesterone levels, or any combination of the aforementioned. As an example for cancers exhibiting testosterone receptors one could use Testred® capsules (ICN), Delatestryl® Injection (BTG), Virilon Injection® (Star) or any other suitable steroid hormone(s) comprising testosterone or methyltestosterone, or androgen derivatives of cyclopentanoperhydrophenanthrene, or any suitable testosterone analog or substitute such as norethanedrolone or stanozolol, or any substance providing means of increasing endogenous testosterone levels, or any combination of the aforementioned compositions.
Reduction to Practice—Chemotherapeutics for Use in Present Invention Preferred embodiment uses S-Phase specific chemotherapeutics, however almost any phase specific chemotherapeutic could be used. Some representative examples of S-phase antimetabolites include, but are not limited to, cytarabine, fluorouracil, gemcitabine, cladribine, fludarabine, pentostatin. Some representative examples of S-Phase topoisomerase inhibitors, include but are not limited to, daunorubicin, doxorubicin, idarubicin, etoposide, teniposide. M phase chemotherapeutic include, but are not limited to, vincristine, vinblastine, vinorelbine, docetaxel, paclitaxel. A more comprehensive list of phase specific chemotherapeutics is contained in Harrison's Principles of Internal Medicine (p. 529 in the 14th edition and pgs. 538–541 in the 15th edition) incorporated herein by reference. These and other phase specific chemotherapeutics are also listed in the Physicians Desk Reference with information to allow their use by one skilled in the art, also incorporated herein by reference. Also, any other S through M phase chemotherapeutics or analogs currently available or to be developed in the future, or any combinations of chemotherapeutics including non-phase specific agents can also be used.

Chemotherapeutics that act to inhibit S phase progression, rather than induce S phase cytotoxicity, should not be used and possibly include agents such as methotrexate.
Reduction to Practice Examples—Selection of Chemotherapeutic The examples below are provided to clarify the use of cancer accelerants as disclosed under present invention. In some of the examples the S-Phase specific chemotherapeutic irinotecan (Camptosar® from Upjohn, PDR 2412–2418) was chosen because the thoroughness of the data presented in the PDR, however any other suitable phase specific chemotherapeutic could be substituted.

Irinotecan is a topoisomerase I inhibitor. Irinotecan is rapidly converted to SN-38, which is ~1,000 times more potent as a topoisomerase inhibitor. DNA acquires torsional strain during DNA synthesis, which if not relieved by topoisomerase I results in strand breakage and damage during the S-Phase of the cell cycle. Mammalian cells cannot effectively repair these double strand breaks.

Camptosar® comes in two administration regimens, 340 mg/m2 which is administered once every 3 weeks and 125 mg/m2 which is administered once every week. TABLE 3 below shows the two doses with their terminal half lives as well as two lower doses for use in examples of present invention with their projected terminal half lives. The average terminal half lives for the two lower doses were computed using linear projection (i.e. y=mx+b format & using the two known points).

TABLE 3

|  | Dose (mg/m2) | Terminal Half Life (hours) |
| --- | --- | --- |
| Prior Art HD | 340 | 21.0 |
| Prior Art LD | 125 | 10.4 |
| Present Invention HD | 100 | 9.2 (projected) |
| Present Invention LD | 60 | 7.2 (projected) |

The average terminal half lives are important in systemic toxicity. Prior art's high dose (HD) regimen of 340 mg has a 21 hour terminal half life, which is close to the hematologic cell cycle time (19–25 hours), which means that ~90+% of hemopoietic cells will also be killed as they pass through the S-Phase during the chemotherapeutic's efficacy period. The prior art low dose (LD) of 125 mg has a 10.4 hour terminal half life which means only ~50% of the hemopoietic cells are killed, a state from which they can recover in roughly one cell cycle (i.e. ~ one day) under the right conditions. However, prior art LD's terminal half life of 10.4 hours is just slightly under the 11 hour cell cycle of gastrointestinal epithelial cells, which would be expected to result in 95% of the gastrointestinal epithelium being killed, causing diarrhea and other potential problems. It would take the gastrointestinal epithelium slightly over 4 cell cycles to fully recover. Present invention's HD of 100 and LD of 60 have terminal half lives well under even the gastrointestinal epithelium cell cycle time. By contrast, present inventions LD would induce only 65% mortality to gastrointestinal epithelium a condition from which these cells could recover in just over 1 cell cycle versus prior art's recovery time of just over 4 cell cycles.

EXAMPLE 1

Reduced Systemic Toxicity and Increase Kill Rates Versus Prior Art

A post menopausal woman with metastatic breast cancer that possesses both estrogen and progesterone receptors is presented for treatment. Flow cytometry reveals more than 60% of cells are in the S-Phase.

Prior art: A prior art Low Dose Chemotherapeutic regimen using an S-Phase chemotherapeutic (using Irinotecan as a representative example of an S-Phase chemotherapeutic) would involve 125 mg/m2 administered weekly over 4 weeks.

Present Invention: Focusing on dose only, under present invention a 60 mg/m2 could be used in conjunction with administration of estradiol and progesterone.

The purpose of the concomitant hormone administration is to accelerate the DNA synthesis rate several fold during the period the S-Phase chemotherapeutic is active. Cutting the dose in half and accelerating the S-Phase activity rate several fold could be used to maintain a high phase specific kill rate at the lower doses. A several fold increase in DNA synthesis would result in several times the amount of torsional strain situations that require relief and subsequently a several fold increase in strand breakage by topoisomerase inhibitors, offsetting the effects of a lower dose. A several fold increase in DNA synthesis would result in a several fold increase in the amount of false substrates such as purine and pyrimidine analogs being incorporated, off-setting the effects of a lower dose. On the other side of the equation, systemic toxicity would be much lower than under prior art.

Likewise, if we were to give this patient the same dose as under prior art in conjunction with the estrogen and progesterone it would also have benefit over prior art. First, the accelerants selectively increase damage to the breast cancer cells because they selectively accelerate the S-Phase of the cancer cells while the chemotherapeutic is active, particularly in women with reduced endogenous hormone levels such as the patient presented. Hemopoietic and gastrointestinal cells are not accelerated. Therefore, under present invention, kill rate is increased, and systemic toxicity remains the same for a distinct advantage over prior art.

EXAMPLE 2A

Boosting M Phase Kill Rate

Cancer accelerants can also be used to synchronize a large wave of cells to come through the M Phase at a given time. By sweeping them out of the S-Phase more quickly, a larger number of them will be moving into the M-Phase within a shorter window of time. Administering an M-Phase chemotherapeutic timed to match this wave of cells as it comes through the M-Phase will increase the tumor kill rate.

Using our 30 day breast cancer example in TABLE 1 and assuming we are on the 5× side of the Gompertzian curve, using cancer accelerants of present invention to release the S-Phase halt would reduce the 17 day S-Phase time to a normal of 6 days (@32% as in the colon baseline) and the 6 days would be adjusted to 1.2 days because we are on the 5× side of the Gompertzian curve (6 days÷5) resulting in the 57% of tumor cells that were in the S-Phase now headed toward the M-Phase over a 1.2 day window. With the Gompertzian effect the G2 phase would now be at 0.7 days (3.5 days÷5), which is when the first cell in the wave could be expected to arrive in the M-Phase followed 1.2 days thereafter by the last cell in the wave. Administration of any M-Phase chemotherapeutic, rationally timed to maximize its kill rate across this wave, would result in a significantly higher kill rate over prior art. The M-Phase typically contains only about 5% of the cells at any given time. Boosting this number to 57% by accelerants of present invention, in conjunction with subsequent administration of M-Phase chemotherapeutics, would be an improvement over prior art.

EXAMPLE 2B

Accelerants and Combination Chemotherapy

Same situation as in example 2A except this time the accelerants are administered in conjunction with an S-Phase chemotherapeutic followed in ≧0.7 days (or other suitable time) by administration of an M-Phase chemotherapeutic.

In this example, both the advantages of the S-Phase and M-Phase as previously described over prior art are obtained in a combination chemotherapeutic administration regimen. Furthermore, combination regimens synchronized to administration of cancer accelerants can also be used to allow short terminal half life chemotherapeutics to be used, compensating for lower kill rates by using the mathematical product of the combined S and M rates (e.g. if each has an in phase kill rate of only 80%, the kill rate of the combined administration is 96% i.e. 20% survive S chemo×20% then survive M chemo=4% survive both). Short terminal half lives also allow for innumerable combinations of regimens that arbitrage the disparity between tumor and hemopoietic cell cycles times to allow high frequency administrations with low levels of hematologic toxicity.

Example 2C
Creating the 100% S-Phase Tumor

By using the concomitant cancer accelerant/phase specific chemotherapeutic administration regimens of present invention followed by subsequent endocrine blocking methods of prior art we can create a 100% S-Phase Tumor. The tumor can be held in this state for extended periods of time (within parameters) and then killed at a chosen time by concomitant cancer accelerants/phase specific chemotherapeutics as proposed under present invention. This is an alternative method to using variable AIs.

In this example we administer our S-Phase cancer accelerant and S-Phase chemotherapeutic followed by administration of tamoxifen (or any other prior art endocrine blocking technique), said administration of tamoxifen beginning after the efficacy period/terminal half life of the chemotherapeutic, and said administration of tamoxifen being discontinued prior to the administration of the next cancer accelerant/chemotherapeutic administration, said discontinuation of tamoxifen occurring not less than the terminal half life of the tamoxifen or other tamoxifen clearance time required to prevent the tamoxifen from interfering with the utility of accelerants as disclosed under present invention. This sequence of administrations would be repeated for several cycles in accordance with the Skipper log cell kill model.

Using our 30 day breast cancer example in TABLE 1 and endocrine accelerants plus chemotherapy of present invention, followed by tamoxifen as described above, and assuming our first tumor kill rate has gotten us to the 5× side of the Gompertzian curve, the following would happen. The duration of all other phases (excluding S) is 13 days,which when accelerated 5× means within ~2.5 days all other cells will have been swept into the S-Phase, and using the tamoxifen to insure the S-phase remains long, the cells will languish there for next 9 to 47 days (depending on the genetic mutation profile of the cancer—i.e how much does the 47 day E-block number in TABLE 1 also succumb to the 5× accelerated growth rate) or until the second administration of concomitant cancer accelerant/phase specific chemotherapeutics as proposed under present invention. Repeated accelerant/chemo administrations followed by tamoxifen followed by accelerant/chemo administration, would yield phase kill rates equal to tumor kill rates. Thus a 99% S-Phase chemotherapeutic would now become a 99% tumor kill rate chemotherapeutic with each application, versus 32% maximum tumor kill rate under prior art. Prior arts attempts to repeat 4 administrations over 4 weeks to achieve the same 99% rate would no longer be necessary.

It should be noted that the use of tamoxifen as disclosed here is primarily intended for women with active menstrual cycles. Post menopausal women, women that have previously undergone surgical castration, or women who have experienced ablation of the ovaries from prior chemotherapeutic regimens may not benefit significantly from endocrine blocking versus accelerant/chemo combinations alone.

Using compositions and methods of present invention will provide a means for appropriately synchronizing the endocrine dependent tumor to the phase specific chemotherapeutic, which is a completely novel and unobvious method over prior art. The utility provided by said method of present invention over prior art will be enormous in that it will yield curative results versus moderately palliative results in the treatment of endocrine dependent cancers.

Example 3
Creation of the 100% S-Phase Tumor for Continuous Administration Regimens Some examples of S-phase specific, continuous administration regimens mentioned under prior art include 30 mg/m2 per day over 120 hours of irinotecan and 0.5 mg/m2 per day of Topotecan over 21 days. Combining cancer accelerants of present invention with these prior art continuous administration regimens would yield a novel administration approach and novel benefits over prior art.

Presumably these regimens use low cell kill rate doses but since endocrine dependent cells spend so much more time in the S-Phase would tend to acquire greater overall genetic damage over one cell cycle than normal rapidly proliferating cells. Unfortunately, an endocrine dependent cancer such as the breast cancer that cycles once every 30 days would not even get through one cell cycle in the 5 days or 21 days mentioned above.

Administration of accelerants could be used to improve the results of continuous regimens in several ways. The first administration of the accelerant would be a high dose aimed at greatly accelerating the endocrine dependent tumor's synthesis rate and progression through the S-Phase which would result in a high kill rate (even at the low dose chemo) and a more rapid initial reduction in tumor size (as the S-phase is where most of the cells are).

The object of this initial large, quick reduction is to get all tumors below the billion cell mass, causing a 5 fold acceleration in progression of cells in all other phases (based on the Gompertzian curve) and sweeping them all into the S-Phase where they will encounter the S-Phase halt or slowdown. In our hypothetical 30 day breast tumor, the duration of all other phases (excluding S) is 13 days,which when accelerated 5× means within ~2.5 days all other cells will have been swept into the S-Phase where they will languish for next 9 to 47 days (as previously explained in example 3 C) or until the second administration of endocrine accelerants. In essence, using endocrine accelerants as disclosed, one can create a virtual 100% S-Phase tumor in a few days. The S-Phase is where they accumulate their damage however, under prior art some of the cells may not even get to the S-Phase for 13 days.

Subsequent administrations of accelerants could be done periodically to further enhance the kill rate.

As an example, if it was determined that after 5 days using the low dose regimen, the S-Phase cells had acquired enough damage to effectively yield a 99% kill rate, another high dose of endocrine accelerants would be administered at that time, followed at the appropriate time by an infusion of a 99% kill rate M-Phase chemotherapeutic. This would effectively constitute two cycles per the Skipper log cell kill model and allow for 4 such double cycles (8 effective Skipper cycles) to be executed under the 21 day low dose regimen described.

Example 4
Preserving Integrity of variable AI Computations

A woman with metastatic breast cancer that possesses estrogen receptors underwent chemotherapy with 30 mg/m2 the S-Phase chemotherapeutic doxorubicin administered once per week for 4 weeks, for 3 cycles. The tumor showed a 32% reduction in size after the regimen, which did not meet the 50% threshold for a partial response.

The woman then underwent surgical castration to slow the growth of her cancer. Based on imaging scans (PET, MRI etc . . . ) it is determined the largest of the several clinically detectable tumors has doubled in size over two months (i.e. ~60 day cell cycle) and is currently ~2 cubic cm (~2 billion cells). Flow cytometry reveals ~78% cells in the S-Phase. Prior to the castration the tumor was doubling every 1 month (30 day cycle). Her median survival is now expected to increase from 2 years to 4 years under prior art, however she desires a curative course.

Under present invention the patient is given the 30 mg/m2 dose of doxorubicin and estrogen is administered continually over the treatment period by transdermal patch. The Administration Interval of the chemotherapeutic is computed in accordance with the formulas and methods previously disclosed in present invention for a variable AI rather than using the standard fixed 7 day administration interval as under prior art.

The use of the variable AI imparts the benefits of insuring the continued synchronization of the phase specific chemotherapeutic to the susceptible phase in the cancer cell population and preventing cells from becoming an asynchronously cycling population again. The inability of prior art's fixed, calender based, AI's to prevent this from happening prevents prior art phase specific chemotherapeutic regimens from achieving curative result as previously discussed.

The primary purpose of administering the S-Phase accelerants in this situation is that it insures the integrity of the computed variable AI across the Gompertzian curve. The comparison in TABLE 1 shows the S-Phase difference that can exist between a normal versus endocrine deprived breast cancer. If the tumor size was reduced below the 1 billion cell level where it cycles 5 times faster, but the S-Phase was still stuck in the 17–47 day range (or some other indeterminate value between 3.4 and 9.4 days from Gompertzian v. cancer mutation profile dynamics) the AI could not be reasonably computed. The five fold Gompertzian rate increase would apply primarily to the 13 days non S-Phase times and indeterminately to the S-Phase, resulting in a distorted cell cycle that would likely differ from any computed AI. Eliminating any endocrine dependent S-Phase halt or slowdown insures the breast cancer follows the accelerated growth rate predicted by a move backward along the Gompertzian curve in accordance with the variable AI administration schemes proposed previously under present invention.

Example 5
Accelerated Regimens in the Comfort of Home

Assume we have an estrogen dependent metastatic cancer and the largest observable mass is 1 cubic cm. Using continuous administration of estrogen would insure the S-Phase is proportionate with all other phases (i.e. it is 32%) and subject to the same Gompertzian acceleration as all other phases. In our 30 day breast cancer in TABLE 1 the first administration takes us into 5x territory, using continuous endocrine administration (e.g. oral, transdermal) would allow us to use a variable AI as computed by methods previously provided. Cells in all other phases than S add up to 13 days, which would be accelerated down to 2.6 days for a total cell cycle time of 3.8 days with 1.2 days for the S-phase. The S-Phase chemotherapeutic Etopophos® (etoposide—from Squibb PDR p. 864) can be administered, orally, daily, at a dose of 50 mg/m2 for 21 days. Taking a daily oral dose comprising 50 mg/m2 of Etopophos® and continuous administration of estradiol would allow us to get through 5 skipper cycles in that 21 day time period, by using endocrine accelerants of present invention and getting into the Gompertzian accelerated growth mode.

Likewise, if we started with the largest observable tumor being 1.5 cubic centimeters, the AI profile with endocrine accelerants would be day 1, 5,6,7,8,9—the additional cycle to account for when all metastatic sites would effectively start the synchronous cycle. Subsequent cycles, assuming no chemotherapeutic vacation or "off period", would be daily, under continuous estradiol administration as proposed by present invention. Up to 450 mg/m2 dose of etoposide would be administered on day one with a single dose of estradiol timed in conjunction with the terminal half life of the chemotherapeutic—this is to get the biggest tumor cut down for its move into the 5x zone with the second administration. The estradiol is not administered continuously between days 1–5 so the S-Phase is deliberately kept slow to minimize regrowth. The second administration (i.e. on day 5) establishes the start of synchronization for all the masses, which are all now in the 5x Gompertzian zone, and estradiol is continuously administered to insure S-Phase compliance with the 5x Gompertzian zone growth rate over the remaining 50 mg/m2 for 21 days as described above.

Other Embodiments and Envisioned Enhancements

The examples presented above represent only a few possibilities of using concomitant cancer accelerants and chemotherapy. Many other embodiments and uses are possible.

Natural hormone levels in the body may also be used in conjunction with compositions and methods of present invention. In a woman with a functional menstrual cycle and an endocrine dependent cancer, deference must be given to the natural hormone spikes and levels present (i.e. see HPIM 14th ed . . . p 2101). These may used additively or inhibitorily.

Many other enhancements may also be made and it is envisioned that other substances that also help facilitate DNA synthesis and progression through the S-Phase may be administered in conjunction with the endocrine cancer accelerants. As an example, folic acid is known to play a crucial role in DNA synthesis and could also be administered to insure that no potential nutrient deprivation situation could arise that would impede the desired progression through the S-Phase.

The examples are presented as guidelines only and are not intended to imply these are the optimal combinations or optimal doses for use. Optimal dosages and timing as determined above would be further refined and corroborated in vivo in animal models and in human clinical trials as is customary under prior art methods.

It should not be inferred that the Gompertzian curve as presented and used will apply to all cancers equally. The genetic mutation profile and cell type will result in variations from the "average" Gompertzian curve used in representative examples of present invention. Accordingly, as more precise Gompertzian curves are characterized for specific mutation profiles and cell types the ability to keep chemotherapeutic regimens more precisely synchronized will provide additional benefits including cure rates approaching 100% to the ability to use chemotherapeutics with even shorter terminal half lives, virtually eliminating systemic toxicity.

Alternatively, the accelerated growth rates and corresponding shorter cell cycle duration can be accurately computed under prior art using PET and positron emitting glucose (or any other suitable imaging technology). PET images cellular processes rather than imaging tissue. Cancers take up large amounts of glucose to fuel their accelerated growth an readily stand out on such scans. More importantly, dead cancer cells don't take up glucose allowing one to see the cell kill rate after chemotherapy. Likewise it would be possible to follow regrowth based on either the intensity of glucose uptake or observable growth in size by the tumor. Several scans taken over the tumor's regrowth phase could be used to determine the accelerated cancer cell cycle time at that tumor size. As an example, if the fastest observed regrowth was a 10% increase in tumor size in 5 hours, that would imply a cancer cell cycle time of 50 hours at that tumor size.

Multiple scans over the course of chemotherapeutic administrations as disclosed in present invention could be used to insure the accuracy of the computations as well as properly characterize the actual accelerated growth rate allowing for on the fly recomputations of AI to insure curative result.

Applicant believes the examples demonstrate novelty and unobviousness and provide great utility over prior art. Applicant believes the examples demonstrate the prior art statement " . . . combinations of chemotherapy with endocrine therapy are not useful" (HPIM 14th ed. p. 566, Endocrine Therapy section) are no longer true under methods of present invention.

REFERENCES CITED

Referred to as "MBOC" in this application: Molecular Biology of the Cell, third edition, Garland Publishing, 1994, Bruce Alberts, Dennis Bray, Julian Lewis, Martin Raff, Keith Roberts, and James Watson.

Referred to as "HPIM" in this application: Harrison's Principles of Internal Medicine, 14th edition, McGraw Hill, 1998, Fauci, Braunwald, Isselbacher, Wilson, Martin, Kasper, Hauser, Longo. and 15th edition, McGraw Hill, 2001, Braunwald, Fauci, Kasper, Hauser, Longo, Jameson Referred to as "PDR" in this application: Physicians' Desk Reference, 54th edition, Medical Economics Company, Inc., 2000, Referred to as "BP" in this application: Biochemical Pathways, John Wiley & Sons, Inc. 1999, Gerhard Michal.

Other

This application is a continuation in part of application Ser. No. 09/490,722 now abandoned.

I claim:

1. A method of treating endocrine dependent cancers comprising administration of endocrine hormone(s) in therapeutically effective amounts to accelerate the proliferation rate of said endocrine dependent cancer, in conjunction with administration of phase specific chemotherapeutic(s), whereby an improved treatment method will be provided.

2. The method of claim 1 wherein when said endocrine dependent cancer is estrogen dependent, then said endocrine hormone(s) are selected from the group consisting of one or more of the following: estradiol, estrogen, estriol, estrone, and synthetic estrogen substitutes including ethinylestradiol and diethylstilbestrol.

3. The method of claim 1 wherein when said endocrine dependent cancer is testosterone dependent, then said endocrine hormone(s) are selected from the group consisting of one or more of the following: testosterone and synthetic testosterone substitutes including norethanedrolone and stanozolol.

4. The method of claim 1 wherein when said endocrine dependent cancer is progesterone dependent, then said endocrine hormone(s) are selected from the group consisting of one or more of the following: progesterone and medroxyprogesterone acetate.

5. A method of treating endocrine dependent cancers comprising administration of endocrine hormone(s) in therapeutically effective amounts to accelerate the proliferation rate of said endocrine dependent cancer, in conjunction with administration of phase specific chemotherapeutic(s), followed by administration of therapeutically effective amounts of endocrine blocker(s) or endocrine downregulator(s), whereby an improved treatment method will be provided.

6. The method of claim 5 wherein said method constitutes one administration cycle and said administration cycle is repeated consecutively 2 or more times.

7. The method of claim 5 wherein said endocrine blocker(s) or endocrine downregulator(s) are administered beginning after the efficacy period or terminal half life of said chemotherapeutic(s), and said administration being discontinued prior to the administration of the next administration of endocrine hormone(s) and phase specific chemotherapeutic(s), said discontinuation occurring not less than the terminal half life of said endocrine blocker(s) or endocrine downregulator(s) or other clearance time required to prevent said endocrine blockers or endocrine downregulators from interfering with the utility of said endocrine hormone(s).

8. The method of claim 5 wherein said endocrine blocker(s) or endocrine downregulator(s) are selected from the group consisting of one or more of the following: anastrozole, tamoxifen, antiestrogens, aromatase inhibitors, progestogens, progesterone, medroxyprogesterone acetate, castration, and adrenalectomy.

* * * * *